(12) United States Patent
Baker et al.

(10) Patent No.: US 12,064,235 B2
(45) Date of Patent: Aug. 20, 2024

(54) DIGITAL QUALIMETRIC BIOMARKERS FOR DETERMINING INFORMATION PROCESSING SPEED

(71) Applicant: Hoffmann-La Roche Inc., Little Falls, NJ (US)

(72) Inventors: Mike Baker, Basel (CH); Shibeshih Mitiku Belachew, Basel (CH); Christian Gossens, Basel (CH); Michael Lindemann, Basel (CH); Jörg Sprengel, Reinach (CH)

(73) Assignee: Hoffman La Roche Inc., Newark, NJ (US)

( * ) Notice: Subject to any disclaimer, the term of this patent is extended or adjusted under 35 U.S.C. 154(b) by 867 days.

(21) Appl. No.: 17/092,263

(22) Filed: Nov. 7, 2020

(65) Prior Publication Data

US 2021/0059572 A1   Mar. 4, 2021

Related U.S. Application Data

(63) Continuation of application No. PCT/EP2019/061819, filed on May 8, 2019.

(30) Foreign Application Priority Data

May 9, 2018   (EP) ..................... 18171567

(51) Int. Cl.
*A61B 5/11*   (2006.01)
*A61B 5/00*   (2006.01)
(Continued)

(52) U.S. Cl.
CPC ............ *A61B 5/1124* (2013.01); *A61B 5/162* (2013.01); *A61B 5/4082* (2013.01);
(Continued)

(58) Field of Classification Search
CPC ..... A61B 5/1124; A61B 5/162; A61B 5/4082; A61B 5/4088; A61B 5/7475; G16H 20/70; G16H 50/20; G16H 50/30
See application file for complete search history.

(56) References Cited

U.S. PATENT DOCUMENTS 5,230,629 A * 7/1993 Buschke ................ G09B 19/00
434/236
2012/0330182 A1 * 12/2012 Alberts .................. G16H 50/30
607/45

(Continued)

FOREIGN PATENT DOCUMENTS

| WO | WO 99/23997 A2 | 5/1999 |
| WO | WO 2018/050746 A1 | 3/2018 |
| WO | WO 2018/050763 A1 | 3/2018 |

OTHER PUBLICATIONS

International Search Report and Written Opinion of the International Searching Authority, PCT/EP2019/061819, Jun. 14, 2019, 13 pages.

(Continued)

*Primary Examiner* — Eric F Winakur
*Assistant Examiner* — Abid A Mustansir
(74) *Attorney, Agent, or Firm* — Bose McKinney and Evans

(57) ABSTRACT

A method for automatically assessing information processing speed in a test subject is disclosed. In the inventive method, a first qualimetric activity parameter for sensorial transmission, cognition and motoric output activity is determined and a second qualimetric activity parameter for sensorial transmission and motoric output activity is determined. A third qualimetric activity parameter for cognition is determined by comparing the first and the second qualimetric activity parameters to each other, and the information processing speed in the test subject is assessed based on the (Continued)

first, second and third qualimetric activity parameters. The information processing speed can be determined by comparing the determined qualimetric activity parameters to a reference and the subject's cognitive impairment can then be determined from the processing speed. The inventive method can be computer implemented. A mobile device or system for carrying out the disclosed methods is also disclosed.

25 Claims, 6 Drawing Sheets

(51) Int. Cl.
    *A61B 5/16*     (2006.01)
    *G16H 20/70*     (2018.01)
    *G16H 50/20*     (2018.01)
    *G16H 50/30*     (2018.01)

(52) U.S. Cl.
    CPC ........... *A61B 5/4088* (2013.01); *G16H 20/70* (2018.01); *G16H 50/20* (2018.01); *G16H 50/30* (2018.01)

(56) References Cited

U.S. PATENT DOCUMENTS

| | | | |
|---|---|---|---|
| 2015/0119731 A1* | 4/2015 | Yasumura | A61B 5/168 434/236 |
| 2019/0200915 A1* | 7/2019 | Baker | A61B 5/486 |

OTHER PUBLICATIONS

Lipsmeier et al., Evaluation of Spmartphone-Based Testing to Generate Explorator Ourcome Measures in a Phase 1 Parkinson's Disease Clinical Trial, Movement Disorders, 2018, vol. 33, No. 8, pp. 1287-1297.
Mariakakis et al., Drunk User Interfaces: Determining Blood Alcohol Level through Everyday Smartphone Tasks, CHI, 2018, 13 pages.
Rao et al., Processing speed test: Validation of a self-administered, iPad®-based tool for screening cognitive dysfunction in a clinic setting, Multiple Sclerosis Journal, 2017, vol. 23, No. 14, pp. 1929-1937.
Smith, Learning Disorders, Special Child Publications, 1968, vol. 3, pp. 83-91.
Costa et al., Information processing speed in multiple sclerosis: Past, present, and future, Multiple Sclerosis Journal, 2017, vol. 23, No. 6, pp. 772-789.

* cited by examiner

DIGITAL QUALIMETRIC BIOMARKERS FOR DETERMINING INFORMATION PROCESSING SPEED

RELATED APPLICATIONS

This application is a continuation of PCT/EP2019/061819, filed May 8, 2019, which claims priority to EP 18 171 567.3, filed May 9, 2018, the entire disclosures of which are hereby incorporated herein by reference.

BACKGROUND

The present disclosure relates to the field of neurological assessments and, in particular, to the assessment of information processing speed in the context of drug research and development, diagnostics and patient and health care management. More specifically, it pertains to a computer-implemented method for automatically assessing information processing speed in a test subject comprising the steps of determining at least one first qualimetric activity parameter for sensorial transmission, cognition and motoric output activity and at least one second qualimetric activity parameter for sensorial transmission and motoric output activity in a preexisting dataset of cognitive oculomotor activity measurements obtained from said test subject, determining at least one third qualimetric activity parameter for cognition by comparing the said first and the said second qualimetric activity parameter to each other, and assessing the information processing speed in a subject based on the at least one first, second and third qualimetric activity parameter. The present disclosure further contemplates a method for determining cognitive impairment in a subject suspected to suffer therefrom comprising determining information processing speed, and determining the cognitive impairment based on the determined information processing speed. The disclosure also provides for a mobile device or system for carrying out the methods of the disclosure as well as the use of said mobile device or system for assessing information processing speed and/or cognitive impairment.

Information processing speed (IPS) is a neurological parameter which indicates the speed with which information is acquired, processed and put into a response. Accordingly, there are different parts of the nervous system involved in information processing speed. The major steps in this process are (1) transmission of afferent visual sensory information, (2) the completion of the cognitive substitution task, and, (3) execution of an efferent motor output (Costa 2017).

Information processing speed can be impaired, accordingly, at different steps. For example, afferent transmission of visual information may be impaired in cases where the afferent nerves are injured or otherwise affected. Similarly, cognition or the efferent motoric output may be impaired.

Cognition and movement diseases and disorders are typically characterized by cognitive impairment and impaired sensory or motoric functions. The diseases and disorders are less frequent but nevertheless typically accompanied by severe complications for the affected patients in daily life.

The diseases and disorders have in common that impaired function of the central nervous system, the peripheral nervous system and the muscular system results in cognition and movement disabilities. The movement disabilities may be primary disabilities due to direct impairments of muscle cells and function or may be secondary disabilities caused by impairments of muscle control by the peripheral and/or central nervous system, in particular, the pyramidal, extrapyramidal, sensory or cerebellar system. The impairment may involve damage, degradation, intoxication or injury of nervous and/or muscular cells.

Typical cognition and movement diseases and disorders include but are not limited to multiple sclerosis (MS), neuromyelitis optica (NMO) and NMO spectrum disorders, stroke, a cerebellar disorder, cerebellar ataxia, spastic paraplegia, essential tremor, myasthenia and myasthenic syndromes or other forms of neuromuscular disorders, muscular dystrophy, myositis or other muscular disorders, a peripheral neuropathy, cerebral palsy, extrapyramidal syndromes, Parkinson's disease, Huntington's disease, Alzheimer's disease, other forms of dementia, leukodystrophies, autism spectrum disorders, attention-deficit disorders (ADD/ADHD), intellectual disabilities as defined by DSM-5, impairment of cognitive performance and reserve related to aging, a polyneuropathy, motor neuron diseases and amyotrophic lateral sclerosis (ALS).

Among the most commonly known and severe diseases and disorders are MS, stroke, Alzheimer's disease, Parkinson's disease, Huntington's disease and ALS.

Multiple sclerosis (MS) is a severe neurodegenerative disease which at present cannot be cured. Affected by this disease are approximately 2 to 3 million individuals worldwide. It is the most common disease of the central nervous system (CNS) that causes prolonged and severe disability in young adults. There is evidence supporting the concept that a B- and T cell-mediated inflammatory process against self-molecules within the white matter of the brain and spinal cord causes the disease. However, its etiology is still not well understood. It has been found that myelin-reactive T cells are present in both MS patients and healthy individuals. Accordingly, the primary abnormality in MS may involve more likely impaired regulatory mechanisms leading to an enhanced T cell activation status and less stringent activation requirements. The pathogenesis of MS includes activation of encephalitogenic, i.e., autoimmune myelin-specific T cells outside the CNS, followed by an opening of the blood-brain barrier, T cell and macrophage infiltration, microglia activation and demyelination. The latter causes irreversible neuronal damage.

Stroke may occur as an ischemic stroke where the blood support is impaired due to obstruction of blood vessels or as hemorrhagic stroke resulting from injury of vessels and bleeding. Signs and symptoms of a stroke may include typically one-sided movement/motoric or sensory impairments, problems of walking, speaking, hearing, spinning vertigo or abnormalities of vision. Said signs and symptoms often appear immediately or soon after the stroke has occurred. If symptoms last less than one or two hours it is known as a transient ischemic attack. Hemorrhagic strokes may also be accompanied by severe headache. The symptoms of a stroke can be permanent. Long term comorbid complications may include pneumonia or loss of bladder control. The early diagnosis and treatment of stroke is decisive for the outcome. Current stroke diagnosis requires imaging techniques such as magnetic resonance imaging (MRI) scanning, Doppler ultrasound, or angiography, as well as neurological examination by a medical practitioner. There are more than 10 million people affected by stroke every year. In the developed world, stroke management has meanwhile become rather efficient due to stroke units. However, these specialized centers are not present in less developed parts of the world of aside from urban regions. The early detection of the disorder has a major influence on the outcome of stroke in patients. Accordingly, there is a need for early detection of signs and symptoms of stroke even aside from the competent stroke units and hospitals. Beyond stroke detection there is also a crucial need for properly assessing mid- to long-term disability outcomes associated with acute stroke treatment intervention as well as spontaneous and rehabilitation program-related recovery.

Alzheimer's disease is a severe and mortal neurodegenerative disease accompanied by dementia and associated problems. In fact, Alzheimer's disease is responsible for 60 to 70% of all cases of dementia. An early symptom of the disease is a reduced short-term memory. Subsequent symptoms include social symptoms such as withdrawal from family and society, as well as physical symptoms such as loss of body functions. Diagnosis of Alzheimer's disease is based on imaging techniques such as CT, MRI, SPECT or PET. Moreover, neurological assessments are carried out by medical practitioners including tests for assessment of cognitive functions. Typical tests include tests where people are instructed to copy drawings similar to one shown in a picture, remember words, read, and subtract serial numbers. Usually, caregivers are required for the diagnosis since the Alzheimer's disease patient him/herself is unaware of his/her deficits. There is no efficient disease-modifying treatment or cure yet for Alzheimer's disease. However, for efficient disease management, a reliable and early diagnosis is helpful. Alzheimer's disease affects about 50 million people worldwide and may be one of the most frequent neurodegenerative diseases in the elderly. Accordingly, there is a need for early detection of signs and symptoms for a proper management of the disease as well as a need for monitoring of disease progression.

Parkinson's disease is a neurodegenerative disease of the central nervous system that pivotally affects the motoric system. Typical symptoms are resting tremor, postural instability, shaking, rigidity, slowness of movement, and difficulties with walking. Dementia and depression and sensory, autonomous nervous system and sleeping problems may also occur at more severe stages of the disease. The motoric problems are caused by degeneration of neurons in the substantia nigra of the midbrain resulting in a significant alteration of dopaminergic neurotransmission. There is no cure for the Parkinson's disease available yet. Diagnosis of Parkinson's disease is based on neurological assessments together with imaging methods, such as CT, MRI, PET or SPECT scanning. Neurological criteria for the diagnosis of the disease include the assessment of bradykinesia, rigidity, resting tremor and postural instability. Recently, assessments of Parkinson's disease using digitally acquired neurological performance parameters have been reported (Lipsmeier 2018).

More than 50 million people are affected by Parkinson's disease. There is a need for an early and reliable diagnosis of this neurodegenerative disease as well as monitoring disease progression.

Huntington's disease is an inherited disorder that results in death of neurons in the central nervous system and, in particular, in the brain. The earliest symptoms are often subtle problems with mood or mental abilities. However, general impairment of coordination and an unsteady gait typically occurs afterwards. In its advanced stages, uncoordinated body movements become apparent and physical abilities gradually worsen until coordinated movement becomes difficult and the person is unable to speak. The cognitive capabilities are also impaired and may decline into dementia. The specific symptoms may, however, individually vary. There is no cure for Huntington's disease available yet. Since Huntington's disease is inherited in a dominant autosomal manner, genome testing for CAG repeats in the huntingtin (HTT) alleles is recommended for individuals being genetically at risk, i.e., patients with a corresponding family history of the disease. Moreover, diagnosis of the disease involves DNA analysis but also imaging methods such as CT, MRI, PET or SPECT scanning, in order to determine cerebral atrophy as well as neurological assessment by a medical practitioner. In particular, the neurological assessments can be carried out according to the criteria for the unified Huntington's disease rating scale system. Huntington's disease is less frequent than Alzheimer's disease and Parkinson's disease. However, it is still a cognition and movement disease or disorder affecting a significant proportion of people with severe and life-threatening complications. There is a need for an early and reliable diagnosis of this neurodegenerative disease as well as monitoring disease progression.

ALS is a neurodegenerative disease that involves cell death of the lower and upper motor neurons that control voluntary muscle contraction. ALS is characterized by stiff muscles, muscle twitching, amyotrophy, and gradually worsening weakness due to muscles decreasing in size resulting in difficulties in walking, speaking, swallowing, and breathing. Respiratory failure is usually the cause of death in patients suffering from ALS. There is no cure yet available for this mortal disease. The diagnosis of ALS is difficult and requires ruling out other possible causes of symptoms and signs such as muscle weakness, muscle atrophy, impaired swallowing or breathing, cramping, or stiffness of affected muscles, and/or slurred and nasal speech. Besides neurological assessment by medical practitioners, the diagnosis typically involves EMG, measuring nerve conductive velocity or Mill. Laboratory tests including muscle biopsy are also available.

Assessing information processing speed will help in the clinical assessments of all of the aforementioned cognition and movement diseases and disorders. In particular, there is a need for the identification of subclinical, subtle changes and measuring the effects of disease modifying treatments (DMTs).

Other aspects of life may also require the assessment of information processing speed as a neurological parameter. For example, testing of cognitive capabilities of an apparently healthy individual, e.g., in the context of educational programs, may also be based on assessments of information processing speed.

The symbol digit modalities test (SDMT, Smith 1968) or the processing speed test (PST, Rao 2017) are tests for measuring information processing speed. Since the past decade SDMT has been widely accepted and used as simple, cheap and sensitive test to assess information processing speed in patients. In 2017, the Multiple Sclerosis Outcome Assessments Consortium (MSOAC) recommended SDMT as a standard test for cognitive decline in MS patients. Until today, SDMT has been applied in paper form, either where patients write responses (wSDMT) or oral form, where the patient speaks out loud (oSDMT) and the investigator notes down the responses.

However, both tests are unable to dissect the different stages of information processing. Since it is possible that reduced velocity in information processing in one step is compensated by increased velocity in another step, measuring information processing speed in the entirety may result in false assessments and diagnoses of disorders or diseases associated with impaired information processing speed. In particular, cognition may be assessed based on wrong data.

Thus, there is a need for the correct and efficient assessment of information processing speed under clinical and social aspects of life. Such an assessment can be carried out in a simple manner during daily life situations by the affected patients.

SUMMARY

The present disclosure relates to a computer-implemented method for automatically assessing information processing speed in a test subject comprising the steps of:
1. determining at least one first qualimetric activity parameter for sensorial transmission, cognition and motoric output activity and at least one second qualimetric activity parameter for sensorial transmission and motoric output activity in a preexisting dataset of cognitive oculomotor activity measurements obtained from said test subject;
2. determining at least one third qualimetric activity parameter for cognition by comparing the said first and the said second qualimetric activity parameter to each other; and
3. assessing the information processing speed in a subject based on the at least one first, second and third qualimetric activity parameter.

In some embodiments, the method may also comprise, prior to step (a), the step of obtaining from the subject using a mobile device cognitive oculomotor activity measurements during a predetermined activity performed by the subject. However, typically the method is an ex vivo method carried out on an existing dataset of cognitive oculomotor activity measurements of a subject which does not require any physical interaction with the said subject, i.e., a method of data analysis and evaluation performed on an existing dataset.

The method according to the present disclosure includes a method which essentially consists of the aforementioned steps or a method which may include additional steps.

The method may be carried out on a mobile device by the subject once the dataset of cognitive oculomotor activity measurements has been acquired. Thus, the mobile device acquiring the dataset and the device evaluating the dataset may be physically identical, i.e., the same device. Such a mobile device will have a data acquisition unit which typically comprises means for data acquisition, i.e., means which detect or measure either quantitatively or qualitatively physical parameters and transform them into electronic signals transmitted to the evaluation unit in the mobile device used for carrying out the method according to the disclosure. The data acquisition unit comprises means for data acquisition, i.e., means which detect or measure either quantitatively or qualitatively physical parameters and transform them into electronic signals transmitted to the device being remote from the mobile device and used for carrying out the method according to the disclosure. Typically, said means for data acquisition comprise at least one sensor. It will be understood that more than one sensor can be used in the mobile device, i.e., at least two, at least three, at least four, at least five, at least six, at least seven, at least eight, at least nine or at least ten or even more different sensors. Typical sensors used as means for data acquisition are sensors such as a gyroscope, magnetometer, accelerometer, proximity sensors, thermometer, humidity sensors, pedometer, heart rate detectors, fingerprint detectors, touch sensors, voice recorders, light sensors, pressure sensors, location data detectors, cameras, time recorders and the like. The evaluation unit typically comprises a processor and a database as well as software which is tangibly embedded in said device and, when running on said device, carries out the method of the disclosure. More typically, such a mobile device may also comprise a user interface, such as a screen, which allows for providing the result of the analysis carried out by the evaluation unit to a user.

Alternatively, the method of the disclosure may be carried out on a device being remote with respect to the mobile device that has been used to acquire the said dataset. In this case, the mobile device shall merely comprise means for data acquisition, i.e., means which detect or measure either quantitatively or qualitatively physical parameters and transform them into electronic signals transmitted to the device being remote from the mobile device and used for carrying out the method according to this disclosure. Typically, said means for data acquisition comprise at least one sensor. It will be understood that more than one sensor can be used in the mobile device, i.e., at least two, at least three, at least four, at least five, at least six, at least seven, at least eight, at least nine or at least ten or even more different sensors. Typical sensors used as means for data acquisition are sensors such as gyroscope, magnetometer, accelerometer, proximity sensors, thermometer, humidity sensors, pedometer, heart rate detectors, fingerprint detectors, touch sensors, voice recorders, light sensors, pressure sensors, location data detectors, cameras, time recorders and the like. Thus, the mobile device and the device used for carrying out the method of the disclosure may be physically different devices. In this case, the mobile device may communicate with the device used for carrying out the method of the present disclosure by any means for data transmission. Such data transmission may be achieved by a permanent or temporary physical connection, such as coaxial, fiber, fiber-optic or twisted-pair, 10 BASE-T cables. Alternatively, it may be achieved by a temporary or permanent wireless connection using, e.g., radio waves, such as Wi-Fi, LTE, LTE-advanced or Bluetooth. Accordingly, for carrying out the method of the present disclosure, the only requirement is the presence of a dataset of cognitive oculomotor activity measurements obtained from a subject using a mobile device. The said dataset may also be transmitted or stored from the acquiring mobile device on a permanent or temporary memory device which subsequently can be used to transfer the data to a remote device used for carrying out the method of the present disclosure. The remote device which carries out the method of the disclosure in this setup typically comprises an evaluation unit comprising a processor and a database as well as software which is tangibly embedded in said device and, when running on said device, carries out the method of the disclosure. More typically, the said device may also comprise a user interface, such as a screen, which allows for providing the result of the analysis carried out by the evaluation unit to a user. Thus, the mobile device and the remote device in this setup form a system for carrying out the method of the disclosure.

The term "computer-implemented" as used herein means that the method according to the present disclosure is carried out automatically by a data processing device such as the evaluation unit describe above being, more typically, part of a mobile or remote device such as smartphone, smartwatch, wearable sensor, portable multimedia device or tablet computer or a conventional computer.

The term "information processing speed" as used herein refers to a neurological parameter indicating the speed of information processing. Information processing in this instance is composed of different steps, starting with the input of visual information into the sensory system that secondarily extends to the output, i.e., responding by pressing a key on the smartphone touchscreen. The major steps in this process are (1) transmission of afferent visual sensory information, i.e., sensorial transmission, (2) the completion of the cognitive substitution task, i.e., the cognitive information processing, and, (3) execution of an efferent motor output, i.e., the hand motor output. Information processing speed may be affected by cognitive impairments associated with neurological diseases or disorders including those mentioned specifically elsewhere herein or may be an indicator for the cognitive capabilities of a subject.

The term "assessing" as used herein refers to assessing the information processing speed in a subject as a neurological parameter. The term includes absolute and relative determinations of the information processing speed. An absolute determination will be, typically, the determination of a parameter indicating the actual speed of information processing in a subject while a relative determination will be, typically, the determination of information processing speed relative to a reference, e.g., relative to a previously determined information processing speed in the test subject or relative to the information processing speed in a reference subject or a group thereof. As referred to herein, information processing speed comprises typically an assessment of the three major contributors: transmission of afferent visual sensory information, i.e., sensorial transmission, the completion of the cognitive substitution task, i.e., the cognitive information processing, and execution of an efferent motor output, i.e., the hand motor output. The assessment of the three major contributors to information processing speed are reflected by the at least one first, second and third activity parameters to be determined in accordance with the method of the present disclosure. As will be understood by those skilled in the art, such an assessment, although preferred to be, may usually not be correct for 100% of the investigated subjects. The term, however, requires that a statistically significant portion of subjects can be correctly assessed. Whether a portion is statistically significant can be determined by the person skilled in the art using various well known statistic evaluation tools, e.g., determination of confidence intervals, p-value determination, Student's t-test, Mann-Whitney test, etc. Details may be found in Dowdy and Wearden, Statistics for Research, John Wiley & Sons, New York 1983. Typically envisaged confidence intervals are at least 50%, at least 60%, at least 70%, at least 80%, at least 90%, at least 95%. The p-values are, typically, 0.2, 0.1, 0.05. Thus, the method of the present disclosure aids the assessment of information processing speed as a neurological parameter by providing a means for evaluating a dataset of cognitive oculomotor activity measurements.

The assessment of information processing speed, typically, can be made in the context of assessing a disease condition, identification/assessment of subclinical, subtle changes in information processing speed assessing disease modifying therapies and treatments (DTMs), monitoring patients, in particular, in a real life, daily situation and on a large scale, supporting patients with lifestyle and/or therapy recommendations, investigating drug efficacy, e.g., also during clinical trials, facilitating and/or aiding therapeutic decision making, supporting hospital management, supporting rehabilitation measure management, supporting health insurance assessments and management, supporting decisions in public health management, and/or assessing cognitive capabilities in general. It will be understood that the present disclosure also contemplates the use of the aforementioned method for assessing information processing speed for these purposes.

The term "at least one" means that one or more qualimetric activity parameters may be determined in accordance with the disclosure, i.e., at least two, at least three, at least four, at least five, at least six, at least seven, at least eight at least nine, at least ten or even more different parameters. Thus, there is no upper limit for the number of different parameters which can be determined in accordance with the method of the present disclosure. Typically, however, there will be between one and three different parameters per dataset of cognitive oculomotor activity measurements determined.

The term "qualimetric activity parameter" as used herein refers to a parameter which indicates the efficacy of sensorial transmission, cognition and/or motoric output activity or combinations thereof. Typically, such a parameter indicates the quality with which a task can be performed, e.g., the correctness of performed tasks, and the time required for performing a task. Thus, a qualimetric parameter may be, typically, a time parameter, such as the performance time required to complete a task or a time parameter indicating a change in velocity when performing a task, such as improvement in velocity or worsening in velocity.

The qualimetric activity parameters to be analyzed in accordance with the method of the present disclosure are typically derived from a computer-implemented Information Processing Speed (IPS) test.

In an embodiment, the computer implemented IPS test determines at least one first qualimetric activity parameter for sensorial transmission, cognition and motoric output activity in a dataset of cognitive oculomotor activity measurements obtained from a test subject by measuring the response time for symbol matching tasks using test symbols which are not familiar (e.g., no naïve numbers or symbols) to the subject who performs the task. Test symbols which are useful for the IPS test, typically, show little similarity to letters or mathematical notation and should, therefore, also be independent of influences such as cultural background, reading and writing capabilities or educational attainment. Such test symbols can, therefore, also be used for children or subjects with low educational attainment (e.g., those who cannot read). Moreover, in order to improve visual recognition, the test symbols follow a simple design principle with less detail. More typically, the symbols may be designed as symbol pairs having characteristic features at opposite sides of a mirror axis parallel to the reading direction or orthogonal to it (e.g., left/right, up/down features) or as recognizable singleton symbols with rotational symmetry, directional orientation or characteristic edges. Typical test symbols are described and shown in the accompanying Examples below.

The test is performed, typically, by showing the subject on a display the test symbol and a legend which allocates different test symbols shown during the test to naïve numbers or other naïve symbols such as letters. These naïve numbers or other naïve symbols are also present on the keypad such that the subject performing the test can press the key which carries the naïve number or naïve symbol being allocated to the test symbol. It will be understood that the response time in the IPS test for this task depends on the reaction time, the processing time for hand motor output and the time for cognitive information processing.

In this embodiment of IPS testing described before, iterations of fixed test symbol matching sequences wherein each sequence consists of matching tasks for at least 6 different test symbols can be performed. The test symbol matching sequences may also comprise more than 6 and, typically, 7, 8 or 9 different test symbols.

Typically, the said iterations are followed by a new randomized test symbol matching sequence. An improvement in response time between the first and the last iteration indicates cognitive learning capabilities of the subject or a standard test response time and the response time in a randomized symbol matching sequence run. Typically, at least two, at least three, at least four iterations of test symbol matching sequences are performed and, more typically, three test symbol matching sequences are performed. Moreover, during the iterations, typically, the test symbol matching can be carried out as in standard clinical SDM tests. Typically, the legend for the symbols, the size of the symbols, the keypad and other parameters displayed on the mobile device used for carrying out the IPS test are kept at constant conditions as far as the dimension, appearance, contrast, etc. are concerned in order to avoid sensory influences which are not related to the information processing speed. Typical examples for the implementation of an automated IPS test are described in the Examples further below.

The IPS test, in one embodiment, determines at least one second qualimetric activity parameter for sensorial transmission and motoric output activity in a dataset of cognitive oculomotor activity measurements obtained from said test subject by measuring a baseline response time. Typically, said baseline response time can be determined in an embodiment by measuring the time for matching a naïve number or symbol to the matching naïve number or symbol on a keypad of the mobile device. More typically, the naïve number or symbol shall be selected such that the individual which carries out the test can perform the matching without substantial cognitive effort. More typically, numbers from 0 to 9 may be used as naïve numbers. Such a baseline response time using naïve number or symbol matching will be mainly dependent on the reaction time and processing time for hand motor output. Cognitive tasks shall play only a minor role and shall not contribute significantly to the baseline response time.

In an embodiment, thereby, at least one third qualimetric activity parameter for cognition can be determined by comparing the first and the second qualimetric activity parameter to each other, i.e., the determined activity parameters can be de-convoluted by said baseline response time into reaction time and processing time for hand motor output and time for cognitive information processing. For the deconvolution, any suitable mathematical operation may be used. For example, the at least one third parameter may be provided by subtracting the at least one second qualimetric activity parameter from the said at least one first qualimetric activity parameter. It will be understood that first and second parameters of comparable nature will be used, e.g., a time first and second time parameter, a first and second ratio of time parameters or a first and second score parameter, etc.

Thus, in the computer-implemented IPS test run on a mobile device which is used to acquire the qualimetric activity parameters to be analyzed in accordance with the method of the present disclosure the difference in response time between a task comprising reaction time, processing time for hand motor output and time for cognitive information processing (test matching by pressing the respective key on a keypad different non-naïve test symbols as described above to a legend which allocates said different test symbols to naïve numbers or other naïve symbols such as letters) and a task comprising reaction time and processing time for hand motor output (baseline task, typically, matching a naïve number or symbol to the matching naïve number or symbol on a keypad) is determined as one cognitive qualimetric activity parameter being part of the dataset to be analyzed by the method of the disclosure. Moreover, the IPS test also aims at determining learning capabilities by comparing the response time required for performing a test task at the end of an iteration of identical test symbol matching sequences and the response time required for performing a randomized symbol matching sequence run. Typically, this time comparison may also be determined as a qualimetric activity parameter in accordance with the method of the present disclosure.

Accordingly, the present disclosure also provides for a method for assessing information processing speed comprising carrying out steps a) to c) for a dataset of oculomotor activity measurements for a first symbol matching task and a symbol matching task after one or more iterations, and, typically four iterations, of identical symbol matching tasks and determining the difference in information processing speed assessed for the dataset of the said first oculomotor activity measurement and the dataset taken after the iterations. The said difference in speed is an indicator for the cognitive learning capabilities of the subject. An improvement in speed is an indicator for normal or improved cognitive capabilities while a worsening is an indicator for cognitive impairment.

Further typical qualimetric activity parameters derived from the IPS test and captured as continuous outcome variables reflecting intra-test fluctuations that measure cognitive integrity are selected from the group consisting of:
1) the elapsed time before (from n−1) response,
2) the elapsed time before (from n−1) correct response,
3) the elapsed time before (from n−1) incorrect response,
4) the elapsed time between (from prior correct response) correct responses, 5) the elapsed time between (from prior incorrect response) incorrect responses, and
6) the parameters 1), 2), and 3) applied to specific symbols or cluster of symbols when the sequence of symbols is modified to evaluate working memory and learning within the task.

More typically, IPS test derived qualimetric parameters of interest are one or more of the following list:
1. Number of correct responses
    a. Total number of overall correct responses (CR) in 90 seconds
    b. Number of correct responses from time 0 to 30 seconds ($CR_{0-30}$)
    c. Number of correct responses from time 30 to 60 seconds ($CR_{30-60}$)
    d. Number of correct responses from time 60 to 90 seconds ($CR_{60-90}$)
    e. Number of correct responses from time 0 to 45 seconds ($CR_{0-45}$)
    f. Number of correct responses from time 45 to 90 seconds ($CR_{45-90}$)
    g. Number of correct responses from time i to j seconds ($CR_{i-j}$) where i,j are between 1 and 90 seconds and i<j.
2. Number of errors
    a. Total number of errors (E) in 90 seconds
    b. Number of errors from time 0 to 30 seconds ($E_{0-30}$)
    c. Number of errors from time 30 to 60 seconds ($E_{30-60}$)
    d. Number of errors from time 60 to 90 seconds ($E_{60-90}$)
    e. Number of errors from time 0 to 45 seconds ($E_{0-45}$)
    f. Number of errors from time 45 to 90 seconds ($E_{45-90}$)
    g. Number of errors from time i to j seconds ($E_{i-j}$), where ij are between 1 and 90 seconds and i<j.
3. Number of responses
    a. Total number of overall responses (R) in 90 seconds
    b. Number of responses from time 0 to 30 seconds ($R_{0-30}$)
    c. Number of responses from time 30 to 60 seconds ($R_{30-60}$)

d. Number of responses from time 60 to 90 seconds ($R_{60-90}$)
e. Number of responses from time 0 to 45 seconds ($R_{0-45}$)
f. Number of responses from time 45 to 90 seconds ($R_{45-90}$)

4. Accuracy rate
   a. Mean accuracy rate (AR) over 90 seconds: $AR = CR/R$
   b. Mean accuracy rate (AR) from time 0 to 30 seconds: $AR_{0-30} = CR_{0-30}/R_{0-30}$
   c. Mean accuracy rate (AR) from time 30 to 60 seconds: $AR_{30-60} = CR_{30-60}/R_{30-60}$
   d. Mean accuracy rate (AR) from time 60 to 90 seconds: $AR_{60-90} = CR_{60-90}/R_{60-90}$
   e. Mean accuracy rate (AR) from time 0 to 45 seconds: $AR_{0-45} = CR_{0-45}/R_{0-45}$
   f. Mean accuracy rate (AR) from time 45 to 90 seconds: $AR_{45-90} = CR_{45-90}/R_{45-90}$ 5. End of task fatigability indices
   a. Speed Fatigability Index (SFI) in last 30 seconds: $SFI_{60-90} = CR_{60-90}/\max(CR_{0-30}, CR_{30-60})$
   b. SFI in last 45 seconds: $SFI_{45-90} = CR_{45-90}/CR_{0-45}$
   c. Accuracy Fatigability Index (AFI) in last 30 seconds: $AFI_{60-90} = AR_{60-90}/\max(AR_{0-30}, AR_{30-60})$
   d. AFI in last 45 seconds: $AFI_{45-90} = AR_{45-90}/AR_{0-45}$ 6. Longest sequence of consecutive correct responses
   a. Number of correct responses within the longest sequence of overall consecutive correct responses (CCR) in 90 seconds
   b. Number of correct responses within the longest sequence of consecutive correct responses from time 0 to 30 seconds ($CCR_{0-30}$)
   c. Number of correct responses within the longest sequence of consecutive correct responses from time 30 to 60 seconds ($CCR_{30-60}$)
   d. Number of correct responses within the longest sequence of consecutive correct responses from time 60 to 90 seconds ($CCR_{60-90}$)
   e. Number of correct responses within the longest sequence of consecutive correct responses from time 0 to 45 seconds ($CCR_{0-45}$)
   f. Number of correct responses within the longest sequence of consecutive correct responses from time 45 to 90 seconds ($CCR_{45-90}$)

7. Time gap between responses
   a. Continuous variable analysis of gap (G) time between two successive responses
   b. Maximal gap (GM) time elapsed between two successive responses over 90 seconds
   c. Maximal gap time elapsed between two successive responses from time 0 to 30 seconds ($GM_{0-30}$)
   d. Maximal gap time elapsed between two successive responses from time 30 to 60 seconds ($GM_{30-60}$)
   e. Maximal gap time elapsed between two successive responses from time 60 to 90 seconds ($GM_{60-90}$)
   f. Maximal gap time elapsed between two successive responses from time 0 to 45 seconds ($GM_{0-45}$)
   g. Maximal gap time elapsed between two successive responses from time 45 to 90 seconds ($GM_{45-90}$)

8. Time Gap between correct responses
   a. Continuous variable analysis of gap (Gc) time between two successive correct responses
   b. Maximal gap time elapsed between two successive correct responses (GcM) over 90 seconds
   c. Maximal gap time elapsed between two successive correct responses from time 0 to 30 seconds ($GcM_{0-30}$)
   d. Maximal gap time elapsed between two successive correct responses from time 30 to 60 seconds ($GcM_{30-60}$)
   e. Maximal gap time elapsed between two successive correct responses from time 60 to 90 seconds ($GcM_{60-90}$)
   f. Maximal gap time elapsed between two successive correct responses from time 0 to 45 seconds ($GcM_{0-45}$)
   g. Maximal gap time elapsed between two successive correct responses from time 45 to 90 seconds ($GcM_{45-90}$)

9. Fine finger motor skill function parameters captured during IPS test
   a. Continuous variable analysis of duration of touchscreen contacts (Tts), deviation between touchscreen contacts (Dts) and center of closest target digit key, and mistyped touchscreen contacts (Mts) (i.e, contacts not triggering key hit or triggering key hit but associated with secondary sliding on screen), while typing responses over 90 seconds
   b. Respective variables by epochs from time 0 to 30 seconds: $Tts_{0-30}$, $Dts_{0-30}$, $Mts_{0-30}$
   c. Respective variables by epochs from time 30 to 60 seconds: $Tts_{30-60}$, $Dts_{30-60}$, $Mts_{30-60}$
   d. Respective variables by epochs from time 60 to 90 seconds: $Tts_{60-90}$, $Dts_{60-90}$, $Mts_{60-90}$
   e. Respective variables by epochs from time 0 to 45 seconds: $Tts_{0-45}$, $Dts_{0-45}$, $Mts_{0-45}$
   f. Respective variables by epochs from time 45 to 90 seconds: $Tts_{45-90}$, $Dts_{45-90}$, $Mts_{45-90}$ 10. Symbol-specific analysis of performance by single symbol or cluster of symbols
    a. CR for each of the 9 symbols individually and all their possible clustered combinations
    b. AR for each of the 9 symbols individually and all their possible clustered combinations
    c. Gap time (G) from prior response to recorded responses for each of the 9 symbols individually and all their possible clustered combinations
    d. Pattern analysis to recognize preferential incorrect responses by exploring the type of mistaken substitutions for the 9 symbols individually and the 9 digit responses individually 11. Learning and cognitive reserve analysis
    a. Change from baseline (baseline defined as the mean performance from the first 2 administrations of the test) in CR (overall and symbol-specific as described in (10)) between successive administrations of IPS tests
    b. Change from baseline (baseline defined as the mean performance from the first 2 administrations of the test) in AR (overall and symbol-specific as described in (10)) between successive administrations of IPS tests
    c. Change from baseline (baseline defined as the mean performance from the first 2 administrations of the test) in mean G and GM (overall and symbol-specific as described in (10)) between successive administrations of IPS tests
    d. Change from baseline (baseline defined as the mean performance from the first 2 administrations of the test) in mean Gc and GcM (overall and symbol-specific as described in (10)) between successive administrations of IPS tests
e. Change from baseline (baseline defined as the mean performance from the first 2 administrations of the test) in $SFI_{60-90}$ and $SFI_{45-90}$ between successive administrations of IPS tests
f. Change from baseline (baseline defined as the mean performance from the first 2 administrations of the test) in $AFI_{60-90}$ and $AFI_{45-90}$ between successive administrations of IPS tests
g. Change from baseline (baseline defined as the mean performance from the first 2 administrations of the test) in Tts between successive administrations of IPS tests
h. Change from baseline (baseline defined as the mean performance from the first 2 administrations of the test) in Dts between successive administrations of IPS tests
i. Change from baseline (baseline defined as the mean performance from the first 2 administrations of the test) in Mts between successive administrations of IPS tests The term "dataset of oculomotor activity measurements" as used herein refers to the entirety of data acquired by the mobile device from a subject during cognitive oculomotor activity measurements or any subset of said data useful for deriving a qualimetric activity parameter. Details are also found elsewhere herein. In particular, the activity measurements in connection with the term "dataset of cognitive oculomotor activity measurements" as used in accordance with the present disclosure comprise measurements of datasets during performance of an Information Processing Speed (IPS) test as described in the accompanying examples, below. In an embodiment of the method of the present disclosure, the dataset of cognitive oculomotor activity measurements comprises data from an Information Processing Speed (IPS) test performed on the mobile device. Typically, said mobile device is comprised in a smartphone, smartwatch, wearable sensor, portable multimedia device or tablet computer. The dataset is a preexisting dataset, which means that the method of the disclosure does typically not require data acquisition from the subject.

The term "subject" as used herein refers to animals and, typically, to mammals. In particular, the subject is a primate and, most typically, a human. The subject in accordance with the present disclosure may suffer from or is suspected to suffer from cognitive impairment which may accompany a disease or disorder as described elsewhere herein. Alternatively, the subject may be a healthy subject to be tested for cognitive capabilities.

Typically, assessing the information processing speed in a subject comprises comparing the determined qualimetric activity parameters to references, whereby the information processing speed will be assessed.

The term "reference" as used herein refers to a discriminator for the determined qualimetric activity parameter which allows for assessing the information processing speed. Such a discriminator may be a value for the qualimetric activity parameter which is indicative of a predefined information processing speed, e.g., the mean or average information processing speed to be expected for a subject, a previously determined information processing speed in the test subject or a value for the information processing speed being indicative of cognitive impairment or healthy condition. In an embodiment of the method of the present disclosure, said references are at least one qualimetric activity parameter as referred to herein derived from a dataset of cognitive oculomotor activity measurements obtained from a reference subject or group thereof.

In an embodiment, a reference qualimetric parameter as referred to herein may be derived from a dataset of oculomotor activity measurements from one or more subjects with assessed information processing speed. Typically, said assessed information processing speed may be information processing speed being in a normal range, i.e., the range of a heathy subject, or being associated with cognitive impairment.

Thus, in an embodiment, the reference qualimetric parameter(s) is/are derived from a dataset of oculomotor activity measurements of a subject or group of subjects known to have normal information processing speed. Typically, a qualimetric activity parameter from the test subject being essentially identical or improved compared to such reference qualimetric activity parameters is indicative of normal information processing speed. Typically, said normal information processing speed is associated with a healthy condition in the test subject.

In yet another embodiment, the reference qualimetric parameter(s) is/are derived from a dataset of oculomotor activity measurements of a subject or group of subjects known to have impaired information processing speed. Typically, a qualimetric activity parameter from the test subject being essentially identical or worsened compared to such reference qualimetric activity parameters is indicative of impaired information processing speed. Typically, said impaired information processing speed is associated with cognitive impairment in said test subject. More typically, the test subject may suffer from one or more of the diseases or disorders referred to elsewhere herein.

Moreover, the reference qualimetric activity parameter may be derived from a dataset of oculomotor activity measurements of the test subject obtained at an earlier stage. Typically, an information processing speed determined from the test subject at a later stage being worsened indicates worsening of information processing speed in the test subject and, thereby, worsening of a pre-existing cognitive impairment and/or diseases or disorders associated therewith or the occurrence of cognitive impairment and/or diseases or disorders associated therewith. Also typically, an information processing speed determined from the test subject at a later stage being improved indicates improvement of information processing speed in the test subject and, thereby, improvement of a pre-existing cognitive impairment and/or diseases or disorders associated therewith. Unchanged information processing speed, typically, indicates unchanged conditions.

Comparing a determined at least one qualimetric parameter, as referred to herein, to a reference can be achieved by an automated comparison algorithm implemented on a data processing device such as a computer. The values of a determined parameter and a reference for said determined parameter are compared to each other as specified elsewhere herein in detail. As a result of the comparison, it can be assessed whether the determined parameter is identical or differs from or is in a certain relation to the reference (e.g., is larger or lower than the reference). Moreover, by determining the degree of difference between a determined parameter and a reference, a quantitative assessment of information processing speed in a subject will be possible.

Moreover, the one or more parameter(s) may also be stored on the mobile device or displayed to the subject, typically, in real time. The stored parameters may be assembled into a time course or similar evaluation measures. Such evaluated parameters may be provided to the subject as a feedback for activity capabilities investigated in accordance with the method of the disclosure. Typically, such feedback can be provided in electronic format on a suitable display of the mobile device and can be linked to a recommendation for therapy or rehabilitation measures.

Further, the evaluated parameters may also be provided to medical practitioners in doctor's offices or hospitals as well as to other health care providers, such as developers of diagnostic tests or drug developers in the context of clinical trials, health insurance providers or other stakeholders of the public or private health care system.

Typically, the method of the present disclosure for assessing information processing speed in a subject may be carried out as follows:

First, the qualimetric activity parameters are determined from an existing dataset of cognitive oculomotor activity measurements obtained from a test subject. At least one first qualimetric activity parameter for sensorial transmission, cognition and motoric output activity is determined and at least one second qualimetric activity parameter for sensorial transmission and motoric output activity is determined. The parameters may be derived from the dataset after said dataset has been transmitted from the mobile device to an evaluating device, such as a computer, or the dataset may be processed in the mobile device.

Second, a third qualimetric activity parameter for cognition may be determined by comparing the first and the second qualimetric activity parameters to each other by, e.g., using a computer-implemented comparison algorithm carried out by the data processor of the mobile device or by the evaluating device, e.g., the computer.

Third, the information processing speed in a subject is assessed by providing the first, second and third activity parameters and determining their individual contributions to the information processing speed in the subject. The results are, typically, provided to the subject or other person, such as a medical practitioner.

Alternatively, a recommendation for a therapy, such as a drug treatment, or for a certain lifestyle, e.g., a certain nutritional diet, is provided automatically to the subject or other person. To this end, the established assessment is compared to recommendations allocated to different assessments in a database. Once the established assessment matches one of the stored and allocated assessments, a suitable recommendation can be identified due to the allocation of the recommendation to the stored assessment matching the established assessment. Typical recommendations involve therapeutic measures as described elsewhere herein.

Alternatively or in addition, the at least one parameter underlying the assessment will be stored on the mobile device. Typically, it will be evaluated together with other stored parameters by suitable evaluation tools, such as time course assembling algorithms implemented on the mobile device which can assist rehabilitation electronically or therapy recommendation as specified elsewhere herein.

The disclosure, in light of the above, also contemplates in an embodiment a method of assessing information processing speed in a subject comprising the steps of:

a) using a mobile device to obtain from said subject a dataset of oculomotor activity measurements;
b) from said dataset of cognitive oculomotor activity measurements, determining at least one first qualimetric activity parameter for sensorial transmission, cognition and motoric output activity and at least one second qualimetric activity parameter for sensorial transmission and motoric output activity;
c) determining at least one third qualimetric activity parameter for cognition by comparing the said first and the said second qualimetric activity parameter to each other; and
d) assessing the information processing speed in a subject based on the first, second and third qualimetric activity parameters.

As used in the following, the terms "have," "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B," "A comprises B" and "A includes B" may both refer to a situation in which, besides B, no other element is present in A (i.e., a situation in which A solely and exclusively consists of B) and to a situation in which, besides B, one or more further elements are present in entity A, such as element C, elements C and D or even further elements.

Further, as used in the following, the terms "particularly," "more particularly," "specifically," "more specifically," "typically," and "more typically" or similar terms are used in conjunction with additional/alternative features, without restricting alternative possibilities. Thus, features introduced by these terms are additional/alternative features and are not intended to restrict the scope of the claims in any way. The disclosure may, as the skilled person will recognize, be performed by using alternative features. Similarly, features introduced by "in an embodiment of the disclosure" or similar expressions are intended to be additional/alternative features, without any restriction regarding alternative embodiments of the disclosure, without any restrictions regarding the scope of the disclosure and without any restriction regarding the possibility of combining the features introduced in such way with other additional/alternative or non-additional/alternative features of the disclosure.

The symbol digit modalities test (SDMT, Smith 1968, 1982) or the processing speed test (PST, Rao 2017) do not account for any measurement of the relative weight of the reaction time or motor output time in the overall test performance. In accordance with the method of the present disclosure, advantageously, a computer-implemented IPS test can be applied to determine baseline, cognitive and information processing speed, as well as oculomotor and motor function qualimetric activity parameters. Thereby, a response time for performing a task on the mobile device may be dissected and the contribution of the individual parts of the nervous system being involved in the response can be determined. This is particularly advantageous since it has been found that in conventional SDMT, parts or functions of the nervous system which are affected by a disease may be compensated by parts or functions which are not affected. Thereby, false negative diagnoses may be established based on SDMT data. For example, a patient suffering from a disease such as MS may compensate a bad hand motor performance by superior cognitive and information processing speed or a bad hand motor performance may mask good information processing speed. When measuring the overall response time for performing an SDMT task, such a patient may not perform worse or may perform only insignificantly worse than a healthy subject even though he or she is suffering from cognitive impairment. Thanks to the method of the present disclosure, false positive or negative assessments of information processing speed and, as a consequence thereof, wrong clinical diagnoses with respect to cognitive impairment can be avoided.

Accordingly, the method of the present disclosure may be used for:

- assessing the disease condition;
- identification/assessment of subclinical, subtle changes in information processing speed;
- assessing disease modifying therapies and treatments (DTMs);
- monitoring patients, in particular, in a real life, daily situation and on a large scale;
- supporting patients with lifestyle and/or therapy recommendations;
- investigating drug efficacy, e.g., also during clinical trials;
- facilitating and/or aiding therapeutic decision making;
- supporting hospital management;
- supporting rehabilitation measure management;
- supporting health insurance assessments and management;
- supporting decisions in public health management; and/or
- assessing cognitive capabilities in general.

In the following, further embodiments based on the advantageous method of the present disclosure will be described. The explanations and definitions for the terms given above apply mutatis mutandis.

The present disclosure further relates to a method for determining cognitive impairment in a test subject suspected to suffer therefrom comprising i) determining information processing speed by carrying out the aforementioned method; and ii) determining the cognitive impairment based on the determined information processing speed.

The aforementioned method is also typically carried out automatically in a computer-implemented manner.

The term "cognitive impairment" as used herein refers to any impairment of cognition that results or is accompanied with cognitive functions of the central nervous system or the peripheral nervous system. Typically, cognitive impairment is associated with a cognition and movement disease or disorder involving the central and/or peripheral nervous system affecting the pyramidal, extrapyramidal, sensory or cerebellar system, or a neuromuscular disease or is a muscular disease or disorder. More typically, said cognition and movement disease or disorder is selected from the group consisting of: multiple sclerosis (MS), neuromyelitis optica (NMO) and NMO spectrum disorders, stroke, a cerebellar disorder, cerebellar ataxia, spastic paraplegia, essential tremor, myasthenia and myasthenic syndromes or other forms of neuromuscular disorders, muscular dystrophy, myositis or other muscular disorders, a peripheral neuropathy, cerebral palsy, extrapyramidal syndromes, Parkinson's disease, Huntington's disease, Alzheimer's disease, other forms of dementia, leukodystrophies, autism spectrum disorders, attention-deficit disorders (ADD/ADHD), intellectual disabilities as defined by DSM-5, impairment of cognitive performance and reserve related to aging, Parkinson's disease, Huntington's disease, a polyneuropathy, motor neuron diseases and amyotrophic lateral sclerosis (ALS).

In the aforementioned method of the present disclosure for determining cognitive impairment, information processing speed is determined in a first step by using the method for assessing information processing speed described elsewhere herein.

In a subsequent step, the cognitive impairment is determined based on the information processing speed. Typically, the said determination may comprise the step of comparing the determined information processing speed or the underlying qualimetric activity parameters from the test subject to one or more reference(s) as described elsewhere herein. If the assessment of the information processing speed indicates that information processing speed is impaired, this is typically an indication of cognitive impairment. If the assessment of the information processing speed indicates that information processing speed is in a normal range, this is typically an indication for no cognitive impairment.

In an embodiment of the aforementioned method for determining cognitive impairment, said reference is derived from a dataset of cognitive oculomotor activity measurements of said test subject at a time point prior to the time point when the dataset of cognitive oculomotor activity measurements referred to in step i) has been obtained from the subject.

More typically, a worsening between the determined at least one first, second and/or third qualimetric activity parameter and the reference is indicative of cognitive impairment.

In an embodiment of the aforementioned method for determining cognitive impairment, said reference is derived from a dataset of cognitive oculomotor activity measurements of a subject or group thereof known to suffer from cognitive impairment.

More typically, a determined at least one first, second and/or third qualimetric activity parameter being essentially identical compared to the reference is indicative of a subject that suffers from cognitive impairment.

In an embodiment of the aforementioned method for determining cognitive impairment, said reference is derived from a dataset of cognitive oculomotor activity measurements of a subject or group thereof known not to suffer from cognitive impairment.

More typically, a determined at least one first, second and/or third qualimetric activity parameter being worsened compared to the references is indicative of a subject that suffers from cognitive impairment.

The present disclosure also contemplates a computer program, computer program product or computer readable storage medium having tangibly embedded said computer program, wherein the computer program comprises instructions that carry out the method of the present disclosure when run on a data processing device or computer as specified above. Specifically, the present disclosure further encompasses:

- a computer or computer network comprising at least one processor, wherein the processor is adapted to perform the method according to one of the embodiments described herein,
- a computer loadable data structure that is adapted to perform the method according to one of the embodiments described herein when the data structure is executed on a computer,
- a computer script, wherein the computer program is adapted to perform the method according to one of the embodiments described herein when the program is executed on a computer,
- a computer program comprising program means for performing the method according to one of the embodiments described herein when the computer program is executed on a computer or on a computer network,
- a computer program comprising program means according to the preceding embodiment, wherein the program means are stored on a storage medium readable to a computer,
- a storage medium, wherein a data structure is stored on the storage medium and wherein the data structure is adapted to perform the method according to one of the embodiments described herein after having been loaded into a main and/or working storage of a computer or of a computer network, a computer program product having program code means, wherein the program code means can be stored or are stored on a storage medium, for performing the method according to one of the embodiments described herein, if the program code means are executed on a computer or on a computer network, a data stream signal, typically encrypted, comprising a dataset of oculomotor activity measurements obtained from the subject using a mobile device, and a data stream signal, typically encrypted, comprising the at least one qualimetric parameter derived from the dataset of oculomotor activity measurements obtained from the subject using a mobile device.

Moreover, the present disclosure relates to a method for recommending a therapy for a cognitive impairment comprising the steps of the aforementioned method for determining cognitive impairment in a test subject suspected to suffer therefrom and the further step of recommending the therapy if cognitive impairment is determined.

The term "a therapy for cognitive impairment" as used herein refers to all kinds of medical treatments, including drug-based therapies, surgeries, psychotherapy, physical-therapy and the like. The term also encompasses, life-style recommendations, rehabilitation measures, and recommendations of nutritional diets. Typically, the method encompasses recommendation of a drug-based therapy and, in particular, a therapy with a drug known to be useful for the treatment of the cognition and movement disease or disorder. Such drugs may be a therapy with one or more drugs selected from the group consisting of: interferon beta-la, interferon beta-1b, glatiramer acetate, mitoxantrone, natalizumab, fingolimod, teriflunomide, dimethyl fumarate, alemtuzumab, daclizumab, thrombolytic agents, such as recombinant tissue plasmin activator, acetylcholinesterase inhibitors, such as tacrine, rivastigmine, galantamine or donepezil, NMDA receptor atagonists, such as memantine, non-steroidal anti-inflammatory drugs, dopa carboxylase inhibitors, such as levodopa, tolcapone or entacapone, dopamine antagonists, such as bromocriptine, pergolide, pramipexole, ropinirole, piribedil, cabergoline, apomorphine or lisuride, MAO-B inhibitors, such as safinamide, selegiline or rasagiline, amantadine, anticholinergics, tetrabenazine, neuroleptics, benzodiazepines, and riluzole. Moreover, the aforementioned method may comprise in yet another embodiment the additional step of applying the recommended therapy to the subject.

Further, the disclosure relates to a method for determining efficacy of a therapy for cognitive impairment comprising the steps of the aforementioned method for determining cognitive impairment in a test subject suspected to suffer therefrom and the further step of determining a therapy response if cognitive impairment improves or determining a failure of response if the cognitive impairment is worsened or remains unchanged.

An improvement as referred to in accordance with the present disclosure relates to any improvement of cognitive impairment. Likewise, a worsening means any worsening of the cognitive impairment.

Furthermore, the present disclosure relates to a method of monitoring cognitive impairment in a subject comprising determining whether the cognitive impairment improves, worsens or remains unchanged in a subject by carrying out the steps of the method for determining cognitive impairment in a test subject suspected to suffer therefrom at least two times during a predefined monitoring period.

The term "predefined monitoring period" as used herein refers to a predefined time period in which oculomotor activity measurements are carried out at least two times. Typically, such a period may range from days to weeks to months to years depending on the course of disease or disorder progression to be expected for the individual subject. Within the monitoring period, the activity measurements and parameters are determined at a first time point, which is usually the start of the monitoring period, and at least one further time point. However, it is also possible that there are more than one further time point for activity measurements and parameter determination. In any event, the activity parameter(s) determined from the oculomotor activity measurements of the first time point are compared to such parameters of subsequent time points. Based on such a comparison, quantitative differences can be identified which will be used to determine a worsening, improvement or unchanged cognitive impairment during the predefined monitoring period.

The present disclosure also contemplates a mobile device comprising a processor, at least one sensor and a database as well as software which is tangibly embedded on said device and, when running on said device, carries out any one of the aforementioned methods of the disclosure.

The term "mobile device" as used herein refers to any portable device which comprises a sensor and data-recording equipment suitable for obtaining the dataset of oculomotor activity measurements. Typically, the mobile device comprises a sensor for measuring the oculomotor activity. This may also require a data processor and storage unit as well as a display for electronically simulating an activity test on the mobile device. Moreover, from the activity of the subject, data can be recorded and compiled to a dataset which is to be evaluated by the method of the present disclosure either on the mobile device itself or on a second device. Depending on the specific setup envisaged, it may be necessary that the mobile device comprises data transmission equipment in order to transfer the acquired dataset from the mobile device to one or more further devices. Particular well-suited as mobile devices according to the present disclosure are smartphones, smartwatches, wearable sensors, portable multimedia devices or tablet computers. Alternatively, portable sensors with data recording and, optionally, processing equipment may be used.

The present disclosure, further, contemplates a system comprising a mobile device comprising at least one sensor and a remote device comprising a processor and a database as well as software which is tangibly embedded on said device and, when running on said device, carries out any one of the aforementioned methods of the disclosure, wherein said mobile device and said remote device are operatively linked to each other.

Under "operatively linked to each other" it is to be understood that the devices are connected so as to allow data transfer from one device to the other device. Typically, it is envisaged that at least the mobile device which acquires data from the subject is connected to the remote device carrying out the steps of the methods such that the acquired data can be transmitted for processing to the remote device. However, the remote device may also transmit data to the mobile device, such as signals controlling or supervising its proper function. The connection between the mobile device and the remote device may be achieved by a permanent or temporary physical connection, such as coaxial, fiber, fiber-optic or twisted-pair, 10 BASE-T cables. Alternatively, it may be achieved by a temporary or permanent wireless connection using, e.g., radio waves, such as Wi-Fi, LTE, LTE-advanced or Bluetooth. Further details may be found elsewhere in this specification. For data acquisition, the mobile device may comprise a user interface such as screen or other equipment for data acquisition. Typically, the activity measurements can be performed on a screen comprised by a mobile device, wherein it will be understood that the said screen may have different sizes including, e.g., a 5.1 inch screen.

The mobile device or the system of the present disclosure is provided for use in assessing information processing speed and/or cognitive impairment in a subject.

Further, the mobile device and the system of the present disclosure are also provided for use in monitoring a subject suffering from cognitive impairment, in particular, in a real life, daily situation and on a large scale, for investigating drug efficacy, e.g., also during clinical trials, in a subject suffering from a cognition and movement disease or disorder, for facilitating and/or aiding therapeutic decision making for a subject suffering from a cognition and movement disease or disorder, for supporting hospital management, rehabilitation measure management, health insurance assessments and management and/or supporting decisions in public health management with respect to subjects suffering from a cognition and movement disease or disorder or for supporting a subject suffering from a cognition and movement disease or disorder with lifestyle and/or therapy recommendations.

Further particular embodiments are also listed as follows:

Embodiment 1

A computer-implemented method for automatically assessing information processing speed in a test subject comprising the steps of:
 a) determining at least one first qualimetric activity parameter for sensorial transmission, cognition and motoric output activity and at least one second qualimetric activity parameter for sensorial transmission and motoric output activity in a preexisting dataset of cognitive oculomotor activity measurements obtained from said test subject;
 b) determining at least one third qualimetric activity parameter for cognition by comparing the said first and the said second qualimetric activity parameter to each other; and
 c) assessing the information processing speed in a subject based on the at least one first, second and third qualimetric activity parameters.

Embodiment 2

The method of embodiment 2, wherein said assessing the information processing speed in a subject comprises comparing the determined qualimetric activity parameters to references, whereby the information processing speed will be assessed.

Embodiment 3

The method of embodiment 1 or 2, wherein the said dataset of cognitive oculomotor activity measurements comprises data from an Information Processing Speed (IPS) test performed on the mobile device.

Embodiment 4

The method of embodiment 3, wherein said mobile device is comprised in a smartphone, smartwatch, wearable sensor, portable multimedia device or tablet computer.

Embodiment 5

The method of any one of embodiments 2 to 4, wherein said references are at least one first and second and/or third qualimetric activity parameters derived from a dataset of cognitive oculomotor activity measurements obtained from a reference subject or group thereof.

Embodiment: 6

The method of any one of embodiments 1 to 5, wherein said assessing information processing speed further comprises, based on the assessed information processing speed, assessing a disease condition, identification/assessment of subclinical, subtle changes in information processing speed assessing disease modifying therapies and treatments (DTMs), monitoring patients, in particular, in a real life, daily situation and on a large scale, supporting patients with lifestyle and/or therapy recommendations, investigating drug efficacy, e.g., also during clinical trials, facilitating and/or aiding therapeutic decision making, supporting hospital management, supporting rehabilitation measure management, supporting health insurance assessments and management, supporting decisions in public health management, and/or assessing cognitive capabilities in general.

Embodiment 7

A method for determining cognitive impairment in a subject suspected to suffer therefrom comprising
 i) determining information processing speed by carrying out the method of any one of embodiments 2 to 5; and
 ii) determining the cognitive impairment based on the determined information processing speed.

Embodiment 8

The method of embodiment 7, wherein said reference is derived from a dataset of cognitive oculomotor activity measurements of said test subject at a time point prior to the time point when the dataset of cognitive oculomotor activity measurements referred to in step i) has been obtained from the subject.

Embodiment 9

The method of embodiment 8, wherein a worsening between the determined at least one first, second and/or third qualimetric activity parameter and the references is indicative of cognitive impairment.

Embodiment 10

The method of embodiment 7, wherein said reference is derived from a dataset of cognitive oculomotor activity measurements of a subject or group thereof known to suffer from cognitive impairment.

Embodiment 11

The method of embodiment 10, wherein determined at least one first, second and/or third qualimetric activity parameter being essentially identical compared to the reference is indicative of a subject that suffers from cognitive impairment.

Embodiment 12

The method of embodiment 7, wherein said reference is derived from a dataset of cognitive oculomotor activity measurements of a subject or group thereof known not to suffer from cognitive impairment.

Embodiment 13

The method of embodiment 12, wherein determined at least one first, second and/or third qualimetric activity parameter being worsened compared to the references is indicative of a subject that suffers from cognitive impairment.

Embodiment 14

The method of any one of embodiments 7 to 13, wherein said cognitive impairment is associated with a cognition and movement disease or disorder involving the central and/or peripheral nervous system affecting the pyramidal, extrapyramidal, sensory or cerebellar system, or a neuromuscular disease or is a muscular disease or disorder.

Embodiment 15

The method of embodiment 14, wherein said cognition and movement disease or disorder is selected from the group consisting of: multiple sclerosis (MS), neuromyelitis optica (NMO) and NMO spectrum disorders, stroke, a cerebellar disorder, cerebellar ataxia, spastic paraplegia, essential tremor, myasthenia and myasthenic syndromes or other forms of neuromuscular disorders, muscular dystrophy, myositis or other muscular disorders, a peripheral neuropathy, cerebral palsy, extrapyramidal syndromes, Parkinson's disease, Huntington's disease, Alzheimer's disease, other forms of dementia, leukodystrophies, autism spectrum disorders, attention-deficit disorders (ADD/ADHD), intellectual disabilities as defined by DSM-5, impairment of cognitive performance and reserve related to aging, Parkinson's disease, Huntington's disease, a polyneuropathy, motor neuron diseases and amyotrophic lateral sclerosis (ALS).

Embodiment 16

A method for recommending a therapy for a cognitive impairment comprising the steps of the method of any one of embodiments 7 to 15 and the further step of recommending the therapy if cognitive impairment is determined.

Embodiment 17

A method for determining efficacy of a therapy against cognitive impairment comprising the steps of the method of any one of embodiments 7 to 15 and the further step of determining a therapy response if cognitive impairment improves or determining a failure of response if the cognitive impairment is worsened or remains unchanged.

Embodiment 18

A method of monitoring cognitive impairment in a subject comprising determining whether the cognitive impairment improves, worsens or remains unchanged in a subject by carrying out the steps of the method of any one of embodiments 7 to 15 at least two times during a predefined monitoring period.

Embodiment 19

A mobile device comprising a processor, at least one sensor and a database as well as software which is tangibly embedded to said device and, when running on said device, carries out the method of any one of embodiments 1 to 18.

Embodiment 20

A system comprising a mobile device comprising at least one sensor and a remote device comprising a processor and a database, as well as software which is tangibly embedded to said device and, when running on said device, carries out the method of any one of embodiments 1 to 18, wherein said mobile device and said remote device are operatively linked to each other.

Embodiment 21

A mobile device of embodiment 19 or the system of embodiment 20 for use in assessing information processing speed and/or cognitive impairment in a subject.

Embodiment 22

A mobile device of embodiment 19 or the system of embodiment 20 for use in monitoring a subject suffering from cognitive impairment, in particular, in a real life, daily situation and on a large scale, for investigating drug efficacy, e.g., also during clinical trials, in a subject suffering from a cognition and movement disease or disorder, for facilitating and/or aiding therapeutic decision making for a subject suffering from a cognition and movement disease or disorder, for supporting hospital management, rehabilitation measure management, health insurance assessments and management and/or supporting decisions in public health management with respect to subjects suffering from a cognition and movement disease or disorder or for supporting a subject suffering from a cognition and movement disease or disorder with lifestyle and/or therapy recommendations.

Embodiment 23

A mobile device of embodiment 19 or the system of embodiment 20 for use in assessing a disease condition, identification/assessment of subclinical, subtle changes in information processing speed assessing disease modifying therapies and treatments (DTMs), monitoring patients, in particular, in a real life, daily situation and on a large scale, supporting patients with lifestyle and/or therapy recommendations, investigating drug efficacy, e.g., also during clinical trials, facilitating and/or aiding therapeutic decision making, supporting hospital management, supporting rehabilitation measure management, supporting health insurance assessments and management, supporting decisions in public health management, and/or assessing cognitive capabilities in general.

All references cited throughout this specification are herewith incorporated by reference with respect to the specifically mentioned disclosure content as well as in their entireties.

BRIEF DESCRIPTION OF DRAWINGS

The above-mentioned aspects of exemplary embodiments will become more apparent and will be better understood by reference to the following description of the embodiments taken in conjunction with the accompanying drawings, wherein:

FIGS. 5A, 5B and 5C are symbol pairs, FIGS. 5D, 5E and 5F are singletons. FIG. 5A symbol is rounded, allows for strong association, and mirroring matches in reading direction; FIG. 5B symbol is segmented, results in confusing visual inspection, and mirroring in reading direction;

FIG. 5C symbol is strongly edged, allows for strong association, has a prominent mirror axis perpendicular to the reading direction; FIG. 5D symbol has rotational symmetry, allows for easy visual inspection; FIG. 5E symbol is directional and reverse to reading axis; FIG. 5F symbol is edged, has two mirror axes in reading direction.

FIGS. 6A and 6B show examples of IPS test settings on a display of a mobile device. FIG. 6A shows a test for symbol matching and FIG. 6B shows a test for baseline task performance.

DESCRIPTION

Figure 1:
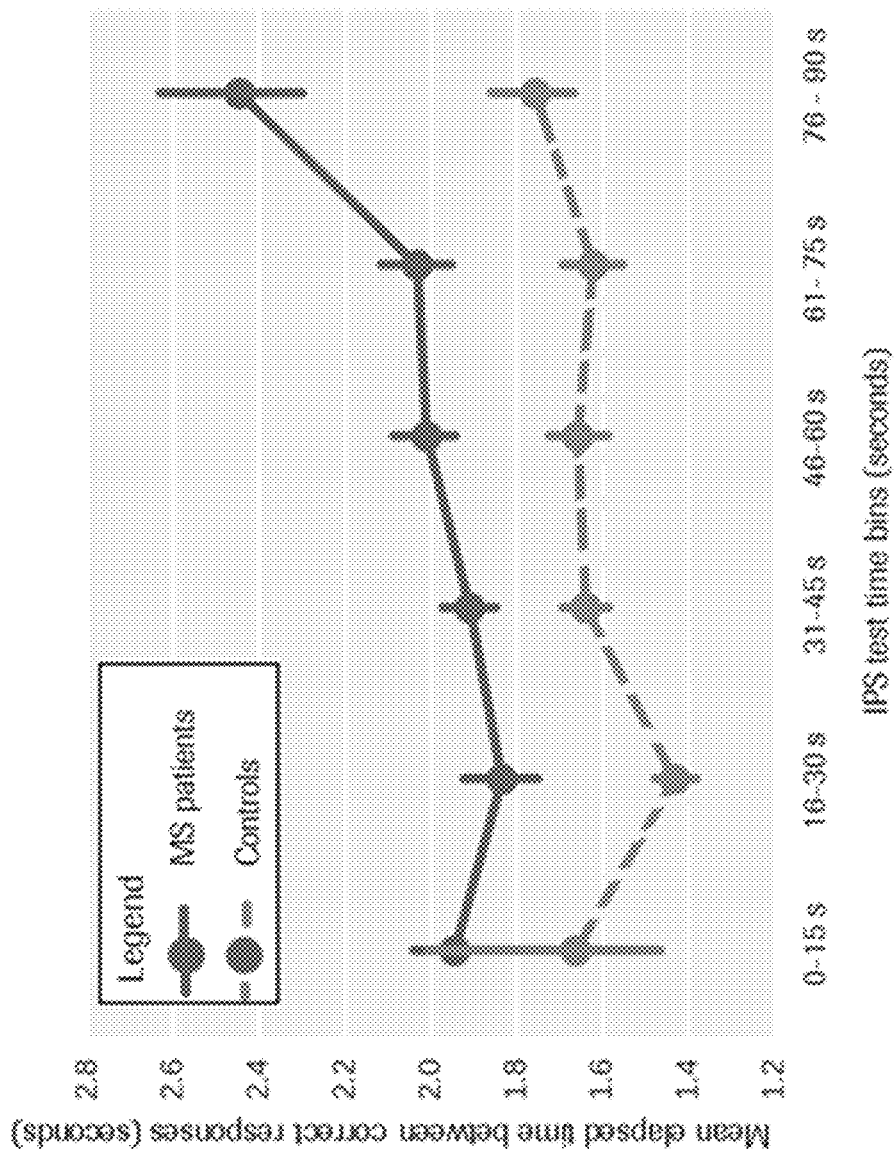
FIG. 1 shows an example of a cognitive qualimetric activity parameter measuring fluctuations of processing speed and correctness in substitution task performance during the IPS test, the elapsed time between correct responses as depicted in the graph (interim analysis of clinical trial NCT02952911) illustrates at the population level a certain degree of intra-test 'fatigability' as a worsening is observed over time during the 90-second IPS test when the performance is monitored and analyzed, in this instance, by 15-second epochs.
Figure 2A:
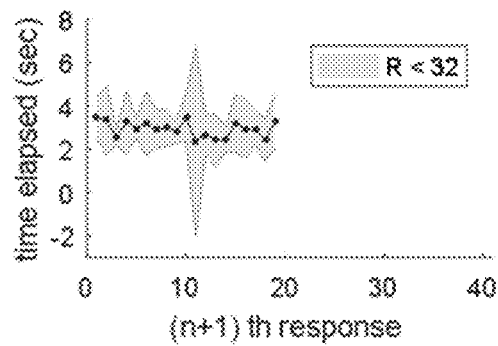
FIGS. 2A-2F show examples of variable temporal profiles of intra-test fluctuations in the time elapsed between overall symbol-digit substitution responses (FIGS. 2A, 2C and 2E) or correct symbol-digit substitution responses (FIGS. 2B, 2D and 2F) in 3 categories of subjects with respect to variable levels of overall IPS performances with a total number of correct responses in 90 seconds of <32 (FIGS. 2A and 2B), 32-39 (FIGS. 2C and 2D), or >40 (2E and 2F).
Figure 2B:
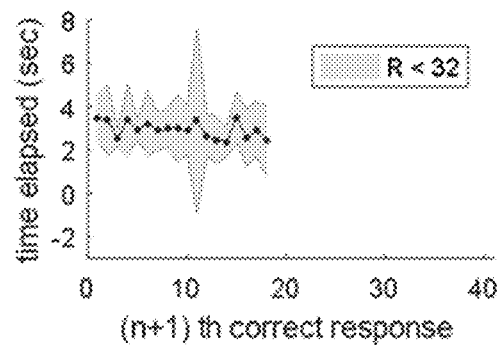
Figure 2C:
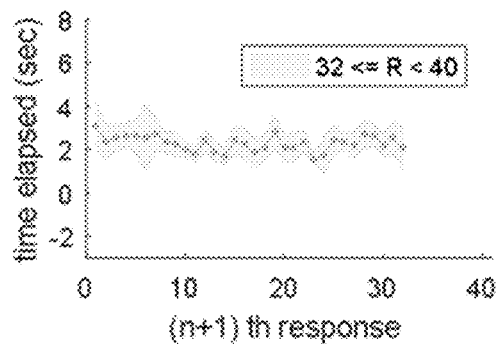
Figure 2D:
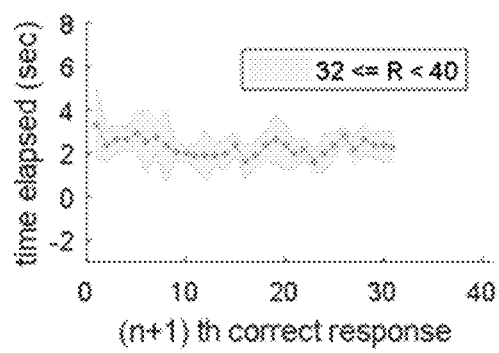
Figure 2E:
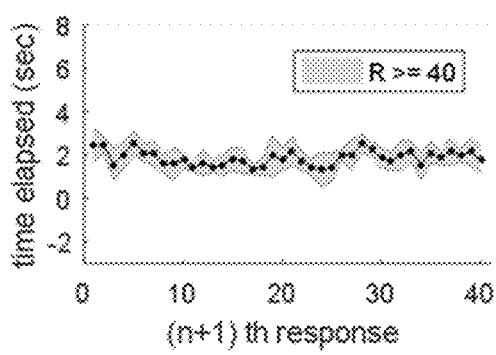
Figure 2F:
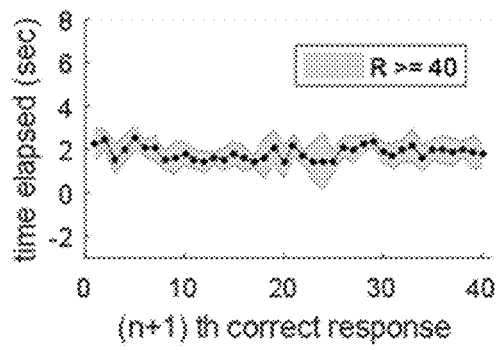

The embodiments described below are not intended to be exhaustive or to limit the invention to the precise forms disclosed in the following detailed description. Rather, the embodiments are chosen and described so that others skilled in the art may appreciate and understand the principles and practices of this disclosure.

Example 1: A Computer-Implemented (Electronic) Cognition—Information Processing Speed (IPS) Test a) IPS Test The aim of the information processing speed testing is to detect impairment of key neurocognitive functions that underlie an iterative visual substitution task, including sustained attention, visual scanning, and recent memory. Information processing in this instance is composed of different steps, starting with the input of visual information into the sensory system that secondarily extends to the output, i.e., responding by pressing a key on the smartphone touchscreen. The major steps in this process are (1) transmission of afferent visual sensory information, (2) the completion of the cognitive substitution task, and, (3) execution of an efferent motor output (Costa 2017).

The symbol digit modalities test (SDMT, Smith 1968) or the processing speed test (PST, Rao 2017) do not account for any measurement of the relative weight of the reaction time or motor output time in the overall test performance. The IPS test has been developed to enable specific assessment of the speed of symbol/digit substitution task by subtracting from the overall performance the reaction time, visual processing time as well as the motor output time, measured separately.

The symbol set of the IPS test consists of 9 different abstract symbols which follow a simple design scheme and are assigned to nine keys, i.e., digits 1 to 9.

To account for participants' reaction time and the time it takes to produce the efferent motor output, a 15-second digit/digit matching exercise will be done after the symbol/digit substitution task. The digits will be presented in an analogue rotation scheme for the numbers as the symbols in the prior substitution task and will be embedded in the same user interface.

For the symbol/digit substitution task of the IPS test, 120 abstract symbols will be displayed in sequence in a maximum of 90 seconds total. The legend key (round Robin alternation of 3 or more versions) showing the nine symbols with their respective matching digits from 1 to 9 will be displayed alongside for reference. The study participant is asked to provide as many correct responses as possible by typing for each iterative symbol the matching key as fast as possible on a numeric keypad on the smartphone's screen during 90 seconds.

The number of correct responses to symbol matching and baseline test will be displayed to the patient.

b) Results

Examples of cognitive qualimetric activity parameters were developed from the above described Information Processing Speed (IPS) test, which is aimed at detecting and measuring impairment of key neurocognitive functions that underlie an iterative visual substitution task, including sustained attention, visual scanning, and recent memory. The digit to symbol substitution tasks are known to correlate with brain atrophy in conditions of mild cognitive impairment and the IPS test performed on a mobile device (differently from similar tests such as SDMT (Smith 1968) or PST (Rao 2017)) enables separate measurement of the cognitive substitution task performance while adjusting for any influence of the visual processing and motor execution time.

As an example of a cognitive qualimetric activity parameter measuring fluctuations of processing speed and correctness in substitution task performance during the IPS test, the elapsed time between correct responses as depicted in FIG. 1 illustrates at the population level a certain degree of intra-test 'fatigability' as a worsening is observed over time during the 90-second IPS test when the performance is monitored and analyzed, in this instance, by 15-second epochs (see FIG. 1).

Variable temporal profiles of intra-test fluctuations in the time elapsed between overall symbol-digit substitution responses (FIGS. 2A, 2C and 2E) or correct symbol-digit substitution responses (FIGS. 2B, 2D and 2F) in 3 categories of subjects with respect to variable levels of overall IPS performances with a total number of correct responses in 90 seconds of <32 (FIGS. 2A and 2B), 32-39 (FIGS. 2C and 2D), or >40 (FIGS. 2E and 2F) are also shown in FIGS. 2A-2F.

Typical examples of cognitive qualimetric activity parameters derived from the IPS test and captured as continuous outcome variables reflecting intra-test fluctuations that measure cognitive integrity are non-exhaustively listed as follows: 1) the elapsed time before (from n−1) response, 2) the elapsed time before (from n−1) correct response, 3) the elapsed time before (from n−1) incorrect response, 4) the elapsed time between (from prior correct response) correct responses, 5) the elapsed time between (from prior incorrect response) incorrect response, 6) the parameters 1), 2), and 3) applied to specific symbols or a cluster of symbols when the sequence of symbols is modified to evaluate working memory and learning within the task.

Importantly, it will be understood that cognitive qualimetric activity parameters as aforementioned can be derived from any other cognitive test acquired from a mobile device and comprising single or composite measures of performance fluctuations in at least one qualitative feature of cognitive functioning and integrity during the completion of a specific cognitive task.

Example 2: A Computer-Implemented IPS Test De-Convoluting Cognition and Estimating Learning A computer-implemented IPS test for smartphone devices was established. In one step, the computer implemented IPS test determines the information processing speed by measuring the response time for symbol matching tasks using test symbols which are not familiar (e.g., no naïve numbers or symbols or symbols which are structurally or symbolically similar) to the patient performing the task. Test symbols which are useful for the IPS test show little similarity to letters or mathematical notation and should, therefore, also be independent of influences such as cultural background, reading and writing capabilities or educational standards. Such test symbols can, therefore, also be used for children or subjects with low educational attainment (e.g., people who cannot read). Moreover, in order to improve visual recognition, the test symbols shall follow a simple design principle with less detail. The symbols may be designed as symbol pairs having characteristic features at opposite sides of a mirror axis (e.g., left/right, up/down features) or as recognizable singleton symbols with rotational symmetry, directional orientation or characteristic edges; see FIGS. 5A-5F.

Figures 6A, 6B:
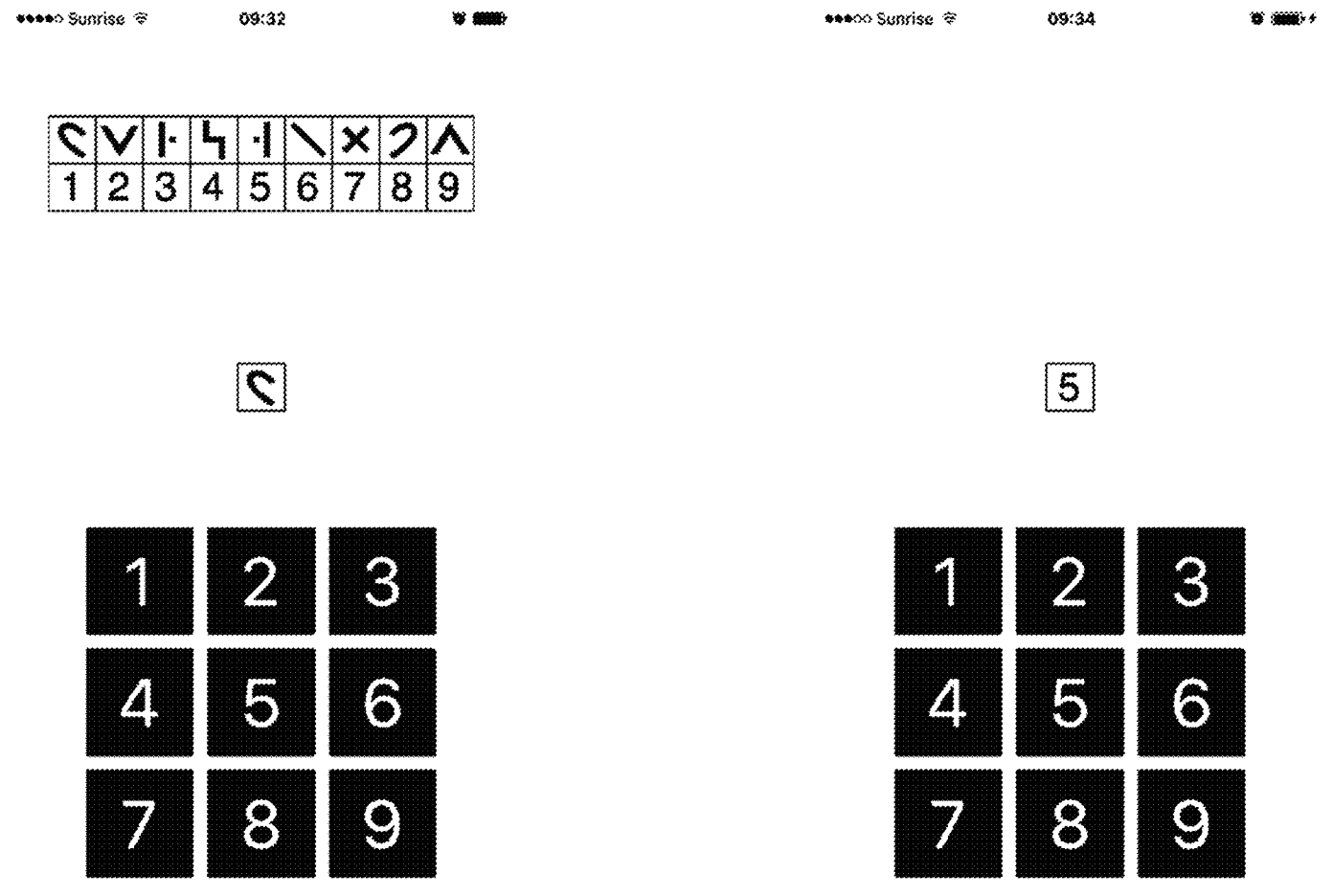

The test is performed by showing the patient on a display the test symbol and a legend which allocates different test symbols shown during the test to naïve numbers or other naïve symbols such as letters. These naïve numbers or other naïve symbols are also present on the keypad such that the subject performing the test can press the key which carries the naïve number or naïve symbol being allocated to the test symbol (see FIGS. 6A-6B). It will be understood that the response time in the IPS test for this task depends on the reaction time, the processing time for hand motor output and the time for cognitive information processing.

Figure 4:
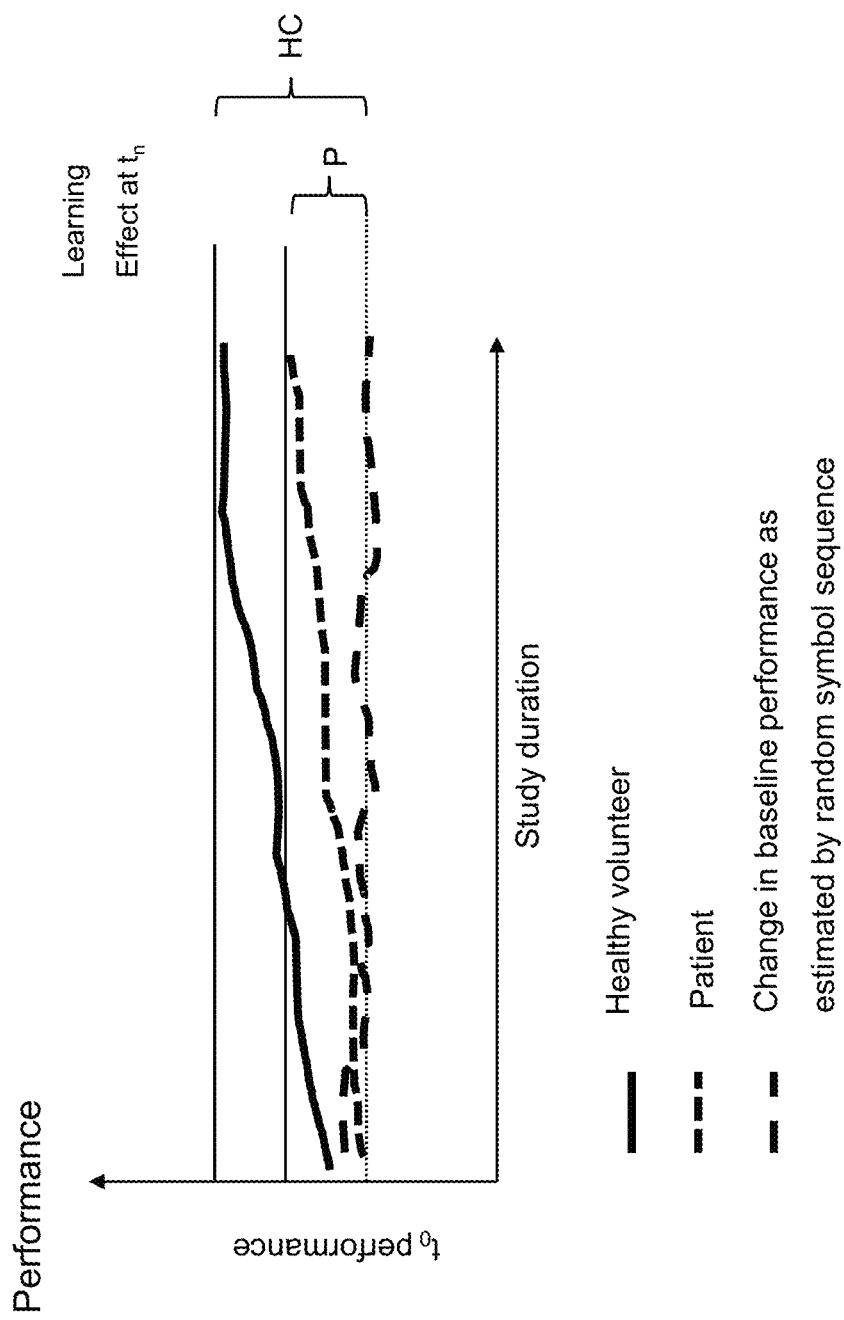
FIG. 4 shows the change in performance observed after several iterations of matching tasks. Performance increases in healthy volunteers and patients for matching tasks while baseline performance remains unaffected.
Figure 5A:
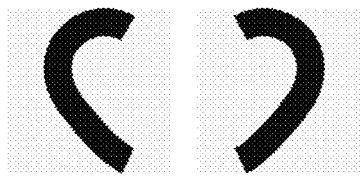
FIGS. 5A-5F show symbols useful for the IPS matching test.
Figure 5B:
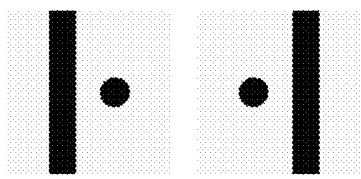
Figure 5C:
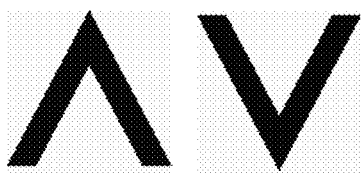
Figure 5D:
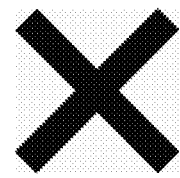
Figure 5E:
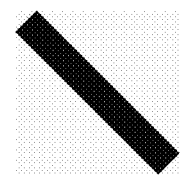
Figure 5F:
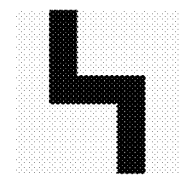

In the step of IPS testing described before, iterations of fixed test symbol matching sequences, wherein each sequence consists of matching tasks for at least 6 different test symbols, can be performed. The said iterations are followed by a new randomized test symbol matching sequence. An improvement in response time between the first and the last iteration indicates cognitive learning capabilities of the subject or a standard test response time and the response time in a randomized symbol matching sequence run. Three test symbol matching sequences are performed before, in the fourth matching sequence run, randomized symbols are shown in the sequence. Moreover, the test symbol matching is carried out as in standard clinical SDMT. The legend for the symbols, the size of the symbols, the keypad and other parameters displayed on the smartphone device used for carrying out the IPS test are kept at constant conditions as far as the dimension, appearance, contrast, etc. are concerned in order to avoid sensory influences which are not related to the information processing speed (see FIGS. 6A and 6B). The IPS test is carried out for 90 seconds. This measurement of velocity prior and after the iterations of identical sequences allows for estimation of the cognitive capabilities, in particular, learning capabilities (see FIG. 4).

Figure 3:
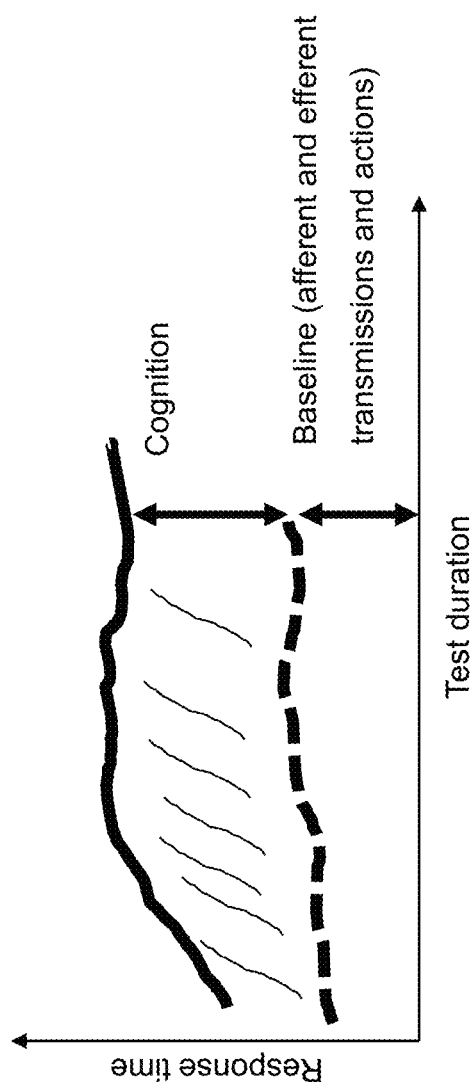
FIG. 3 shows schematically the variation of the response time in total and the baseline variation during the test performance. The difference between baseline and total response time accounts for cognitive activities.

The IPS test in a further step determines a baseline information processing speed by measuring a baseline response time. Said baseline response time is determined by measuring the time for matching a naïve number or symbol to the matching naïve number or symbol on a keypad of the smartphone device (see FIGS. 6A and 6B). The naïve number or symbol shall be selected such that the individual who carries out the test can perform the matching without substantial cognitive effort. More typically, numbers from 0 to 9 may be used as naïve numbers. Such a baseline response time using naïve number or symbol matching shall be mainly dependent on the reaction time and processing time for hand motor output. Cognitive tasks will play only a minor role and shall not contribute significantly to the baseline response time. Thereby, the information processing speed determined in the subsequent steps can be de-convoluted by said baseline response time into reaction time and processing time for hand motor output and time for cognitive information processing (see FIG. 3).

Thus, in the computer-implemented IPS test run on a smartphone device, the difference in response time between a task comprising reaction time, processing time for hand motor output and time for cognitive information processing (e.g., test matching different non-naïve test symbols as described above to a legend which allocates said different test symbols shown during the test to naïve numbers or other naïve symbols such as letters by pressing the respective key on a keypad) and a task comprising reaction time and processing time for hand motor output (baseline task), matching a naïve number or symbol to the matching naïve number or symbol on a keypad is determined as one cognitive qualimetric activity parameter being part of the dataset to be analysed.

The IPS test described before is helpful for the clinical management of patients suffering from multiple sclerosis (MS) since information processing speed is a prevalent cognitive impairment in MS. The test aims at detecting even subtle changes in cognitive functions of MS patients and can be used in clinical settings or self-administration approaches.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

What is claimed is:

1. A method for automatically assessing information processing speed in a test subject, comprising:
   a) obtaining a dataset of cognitive oculomotor activity measurements from the test subject ;
   b) determining a first qualimetric activity parameter for sensorial transmission, cognition and motoric output activity from the dataset of cognitive oculomotor activity measurements, wherein the first qualimetric activity parameter is based on a symbol to digit conversion;
   c) determining a second qualimetric activity parameter for sensorial transmission and motoric output activity from the dataset of cognitive oculomotor activity measurements;
   d) determining a third qualimetric activity parameter for cognition by comparing the first and the second qualimetric activity parameters to each other; and
   e) assessing the information processing speed in the test subject based on the first, second and third qualimetric activity parameters.

2. The method of claim 1, wherein the assessing of the information processing speed in the test subject comprises comparing the determined qualimetric activity parameters to a reference.

3. The method of claim 2, wherein the reference comprises a first, second and/or third reference qualimetric activity parameter(s) derived from a reference dataset of cognitive oculomotor activity measurements obtained from a reference subject or group thereof.

4. The method of claim 1, wherein the first and the second qualimetric activity parameters are taken from a dataset of cognitive oculomotor activity measurements that comprises data from an Information Processing Speed (IPS) test performed on a mobile device.

5. The method of claim 4, comprising providing said mobile device in a smartphone, smartwatch, wearable sensor, portable multimedia device, or tablet computer.

6. A method for determining cognitive impairment in a subject suspected to suffer therefrom, comprising:
   a) obtaining a dataset of cognitive oculomotor activity measurements from the test subject ;
   b) determining a first qualimetric activity parameter for sensorial transmission, cognition and motoric output activity from the dataset of cognitive oculomotor activity measurements, wherein the first qualimetric activity parameter is based on a symbol to digit conversion;
   c) determining a second qualimetric activity parameter for sensorial transmission and motoric output activity from the dataset of cognitive oculomotor activity measurements;
   c) determining a third qualimetric activity parameter for cognition by comparing the first and the second qualimetric activity parameters to each other; and
   d) assessing the information processing speed in the test subject by comparing the determined qualimetric activity parameters to a reference; and
   e) determining the cognitive impairment based on the assessed information processing speed.

7. The method of claim 6, wherein the reference is derived from a dataset of cognitive oculomotor activity measurements of the test subject at a time prior to when the dataset of cognitive oculomotor activity measurements referred to in step a) has been obtained from the test subject.

8. The method of claim 7, wherein a worsening between the first, second and/or third qualimetric activity parameters and the reference is indicative of cognitive impairment.

9. The method of claim 6, wherein the reference is derived from a dataset of cognitive oculomotor activity measurements of a subject or group of subjects known to suffer from cognitive impairment.

10. The method of claim 9, wherein the first, second and/or third qualimetric activity parameters being essentially the same as the reference is indicative of a test subject suffering from cognitive impairment.

11. The method of claim 6, wherein the reference is derived from a dataset of cognitive oculomotor activity measurements of a subject or group of subjects known not to suffer from cognitive impairment.

12. The method of claim 11, wherein the first, second and/or third qualimetric activity parameters being worse than the reference is indicative of the test subject suffering from cognitive impairment.

13. The method of claim 6, wherein said cognitive impairment is associated with a cognition and movement disease or disorder involving the central and/or peripheral nervous system affecting the pyramidal, extrapyramidal, sensory or cerebellar system, or a neuromuscular disease, or is a muscular disease or disorder.

14. The method of claim 13, wherein said cognition and movement disease or disorder is selected from the group consisting of: multiple sclerosis (MS), neuromyelitis optica (NMO) and NMO spectrum disorders, stroke, a cerebellar disorder, cerebellar ataxia, spastic paraplegia, essential tremor, myasthenia and myasthenic syndromes or other forms of neuromuscular disorders, muscular dystrophy, myositis or other muscular disorders, a peripheral neuropathy, cerebral palsy, extrapyramidal syndromes, Parkinson's disease, Huntington's disease, Alzheimer's disease, other forms of dementia, leukodystrophies, autism spectrum disorders, attention-deficit disorders (ADD/ADHD), intellectual disabilities as defined by DSM-5, impairment of cognitive performances and reserve related to aging, Parkinson's disease, Huntington's disease, a polyneuropathy, motor neuron diseases and amyotrophic lateral sclerosis (ALS).

15. A method for recommending a therapy for a cognitive impairment, comprising the method of claim 6 and the further step of recommending the therapy when cognitive impairment is determined.

16. A method for determining efficacy of a therapy against cognitive impairment, comprising the method of claim 6 and the further step of determining a therapy response if cognitive impairment improves or determining a failure of response if the cognitive impairment is worsened or remains unchanged.

17. A method of monitoring cognitive impairment in a subject, comprising determining whether the cognitive impairment improves, worsens or remains unchanged in a subject by carrying out the steps of the method of claim 6 at least two times during a predefined monitoring period.

18. The method of claim 6, wherein the first qualimetric activity parameter is determined using symbols that are not naïve numbers or letters.

19. The method of claim 6, wherein the symbols are selected from the group consisting of symbol pairs having characteristic features at opposite sides of a mirror axis, singleton symbols with rotational symmetry, singleton symbols with directional orientation, and singleton symbols with characteristic edges.

20. A mobile device, comprising:
a processor;
at least one sensor;
a database; and
software embedded on said mobile device, the software configured to:
a) obtain a dataset of cognitive oculomotor activity measurements from the test subject;
b) determine a first qualimetric activity parameter for sensorial transmission, cognition and motoric output activity from the dataset of cognitive oculomotor activity measurements, wherein the first qualimetric activity parameter is based on a symbol to digit conversion;
c) determine a second qualimetric activity parameter for sensorial transmission and motoric output activity from the dataset of cognitive oculomotor activity measurements;
d) determine a third qualimetric activity parameter for cognition by comparing the first and the second qualimetric activity parameters to each other; and
e) assess the information processing speed in the test subject based on the first, second and third qualimetric activity parameters.

21. The mobile device of claim 20, wherein the software is further configured to identify cognitive impairment in a subject.

22. The mobile device of claim 20, the device being configured for monitoring a subject suffering from cognitive impairment in at least one of the following settings: a real life, daily situation; investigating drug efficacy; clinical trials; facilitating and/or aiding therapeutic decision making for a subject suffering from a cognition and movement disease or disorder;
supporting hospital management; rehabilitation measure management; health insurance assessments and management; supporting decisions in public health management; and lifestyle and/or therapy recommendations.

23. A system, comprising:
a mobile device having a sensor; and
a remote device having a processor and a database, and software embedded on the remote device, the software configured to:
a) obtain a dataset of cognitive oculomotor activity measurements from the test subject;
b) determine a first qualimetric activity parameter for sensorial transmission, cognition and motoric output activity from the dataset of cognitive oculomotor activity measurements, wherein the first qualimetric activity parameter is based on a symbol to digit conversion;
c) determine a second qualimetric activity parameter for sensorial transmission and motoric output activity from the dataset of cognitive oculomotor activity measurements;
d) determine a third qualimetric activity parameter for cognition by comparing the first and the second qualimetric activity parameters to each other; and
e) assess the information processing speed in the test subject based on the first, second and third qualimetric activity parameters;
wherein said mobile device and said remote device are operatively linked to each other.

24. The system of claim 23, wherein the software is further configured to identify cognitive impairment in a subject.

25. The system of claim 23, the system being configured for monitoring a subject suffering from cognitive impairment in at least one of the following settings: a real life, daily situation; investigating drug efficacy; clinical trials; facilitating and/or aiding therapeutic decision making for a subject suffering from a cognition and movement disease or disorder;
supporting hospital management; rehabilitation measure management; health insurance assessments and management; supporting decisions in public health management; and lifestyle and/or therapy recommendations.

* * * * *